United States Patent
Wolf et al.

(10) Patent No.: US 6,414,835 B1
(45) Date of Patent: Jul. 2, 2002

(54) CAPACITIVE FILTERED FEEDTHROUGH ARRAY FOR AN IMPLANTABLE MEDICAL DEVICE

(75) Inventors: William D. Wolf, St. Louis Park; James Strom, Arden Hills; Craig L. Wiklund, Bloomington; Mary A. Fraley, Minnetonka; Lynn M. Seifried, Minneapolis, all of MN (US); James E. Volmering; Patrick F. Malone, both of Phoenix, AZ (US); Samuel F. Haq, Mesa, AZ (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/515,385

(22) Filed: Mar. 1, 2000

(51) Int. Cl.[7] .......................... H01G 4/35; H01G 4/228; H01G 4/06
(52) U.S. Cl. .................... 361/302; 361/303; 361/306.3; 361/311; 607/5
(58) Field of Search .......................... 361/301.2, 301.4, 361/302, 303, 306.3, 306.1, 307, 311, 312, 313, 321.1–321.5; 607/5

(56) References Cited

U.S. PATENT DOCUMENTS

| | | | |
|---|---|---|---|
| 4,420,652 A | 12/1983 | Ikeno | 174/52 H |
| 4,991,582 A | 2/1991 | Byers et al. | 128/419 P |
| 5,287,076 A | 2/1994 | Johnescu et al. | 333/182 |
| 5,333,095 A | 7/1994 | Stevenson et al. | 361/302 |
| 5,434,358 A | 7/1995 | Glahn et al. | 174/52.4 |
| 5,470,345 A | 11/1995 | Hassler et al. | 607/36 |
| 5,620,476 A | 4/1997 | Truex et al. | 607/36 |
| 5,650,759 A | 7/1997 | Hittman et al. | 333/182 |
| 5,683,435 A | 11/1997 | Truex et al. | 607/37 |
| 5,685,632 A | 11/1997 | Schaller et al. | 362/205 |
| 5,735,884 A | 4/1998 | Thompson et al. | 607/36 |
| 5,750,926 A | 5/1998 | Schulman et al. | 174/52.3 |
| 5,751,539 A * | 5/1998 | Stevenson et al. | 361/302 |
| 5,759,197 A | 6/1998 | Sawchuk et al. | 607/36 |
| 5,782,891 A | 7/1998 | Hassler et al. | 607/36 |
| 5,825,608 A * | 10/1998 | Duva et al. | 361/302 |
| 5,836,992 A | 11/1998 | Thompson et al. | 607/36 |
| 5,866,851 A | 2/1999 | Taylor et al. | 174/152 |
| 5,867,361 A | 2/1999 | Wolf et al. | 361/302 |
| 5,870,272 A | 2/1999 | Seifried et al. | 361/302 |
| 5,896,267 A | 4/1999 | Hittman et al. | 361/302 |
| 5,905,627 A | 5/1999 | Brendel et al. | 361/302 |
| 5,959,829 A | 9/1999 | Stevenson et al. | 361/302 |
| 5,973,906 A | 10/1999 | Stevenson et al. | 361/302 |
| 5,999,398 A | 12/1999 | Makl | 361/302 |
| 6,008,980 A * | 12/1999 | Stevenson et al. | 361/302 |
| 6,275,369 B1 * | 8/2001 | Stevenson et al. | 361/302 |

* cited by examiner

Primary Examiner—Dean A. Reichard
Assistant Examiner—Eric W. Thomas
(74) Attorney, Agent, or Firm—Girma Wolde-Michael (57) ABSTRACT

A capacitive filtered feedthrough assembly is formed in a solid state manner to employ highly miniaturized conductive paths each filtered by a discoid capacitive filter embedded in a capacitive filter array. A non-conductive, co-fired metal-ceramic substrate is formed from multiple layers that supports one or a plurality of substrate conductive paths and it is brazed to a conductive ferrule, adapted to be welded to a case, using a conductive, corrosion resistant braze material. The metal-ceramic substrate is attached to an internally disposed capacitive filter array that encloses one or a plurality of capacitive filter capacitor active electrodes each coupled to a filter array conductive path and at least one capacitor ground electrode. Each capacitive filter array conductive path is joined with a metal-ceramic conductive path to form a feedthrough conductive path. Bonding pads are attached to the internally disposed ends of each feedthrough conductive path, and corrosion resistant, conductive buttons are attached to and seal the externally disposed ends of each feedthrough conductive path. A plurality of conductive, substrate ground paths are formed extending through the co-fired metal-ceramic substrate between internally and externally facing layer surfaces thereof and electrically isolated from the substrate conductive paths. The capacitor ground electrodes are coupled electrically to the plurality of conductive, substrate ground paths and to the ferrule.

19 Claims, 10 Drawing Sheets

CAPACITIVE FILTERED FEEDTHROUGH ARRAY FOR AN IMPLANTABLE MEDICAL DEVICE

FIELD OF THE INVENTION

This invention relates to electrical feedthroughs of improved design and to their method of fabrication, particularly for use with implantable medical devices.

BACKGROUND OF THE INVENTION

Electrical feedthroughs serve the purpose of providing an electrical circuit path extending from the interior of a hermetically sealed case or housing to an external point outside the case. Implantable medical devices (IMDs) such as implantable pulse generators (IPGs) for cardiac pacemakers, implantable cardioverter/defibrillators (ICDs), nerve, brain, organ and muscle stimulators and implantable monitors, or the like, employ such electrical feedthroughs through their case to make electrical connections with leads, electrodes and sensors located outside the case.

Such feedthroughs typically include a ferrule adapted to fit within an opening in the case, one or more conductor and a non-conductive hermetic glass or ceramic seal which supports and electrically isolates each such conductor from the other conductors passing through it and from the ferrule. The IMD case is typically formed of a biocompatible metal, e.g., titanium, although non-conductive ceramics materials have been proposed for forming the case. The ferrule is typically of a metal that can be welded or otherwise adhered to the case in a hermetically sealed manner.

Typically, single pin feedthroughs supported by glass, sapphire and ceramic were used with the first hermetically sealed IMD cases for IPGs. As time has passed, the IPG case size has dramatically reduced and the number of external leads, electrodes and sensors that are to be coupled with the circuitry of the IPG has increased. Consequently, use of the relatively large single pin feedthroughs is no longer feasible, and numerous multiple conductor feedthroughs have been used or proposed for use that fit within the smaller sized case opening and provide two, three, four or more conductors.

Many different insulator structures and conductor structures are known in the art of multiple conductor feedthroughs wherein the insulator structure also provides a hermetic seal to prevent entry of body fluids through the feedthrough and into the housing of the medical device. The conductors typically comprise electrical wires or pins that extend through a glass and/or ceramic layer within a metal ferrule opening as shown, for example, in commonly assigned U.S. Pat. Nos. 4,991,582, 5,782,891, and 5,866,851 or through a ceramic case as shown in the commonly assigned '891 patent and in U.S. Pat. No. 5,470,345. It has also been proposed to use co-fired ceramic layer substrates that are provided with conductive paths formed of traces and vias as disclosed, for example, in U.S. Pat. Nos. 4,420,652, 5,434,358, 5,782,891, 5,620,476, 5,683,435, 5,750,926, and 5,973,906.

Such multi-conductor feedthroughs have an internally disposed portion configured to be disposed inside the case for connection with electrical circuitry and an externally disposed portion configured to be disposed outside the case that is typically coupled electrically with connector elements for making connection with the leads, electrodes or sensors. The elongated lead conductors extending from the connector elements effectively act as antennae that tend to collect stray electromagnetic interference (EMI) signals that may interfere with normal IMD operations. At certain frequencies, for example, EMI can be mistaken for telemetry signals and cause an IPG to change operating mode.

This problem has been addressed in certain of the above-referenced patents by incorporating a capacitor structure upon the internally facing portion of the feedthrough ferrule coupled between each feedthrough conductor and a common ground, the ferrule, to filter out any high frequency EMI transmitted from the external lead conductor through the feedthrough conductor. The feedthrough capacitors originally were discrete capacitors but presently can take the form of chip capacitors that are mounted as shown in the above-referenced '891, '435, '476, and '906 patents and in further U.S. Pat. Nos. 5,650,759, 5,896,267 and 5,959,829, for example. Or the feedthrough capacitors can take the form of discrete discoidal capacitive filters or discoidal capacitive filter arrays as shown in commonly assigned U.S. Pat. Nos. 5,735,884, 5,759,197, 5,836,992, 5,867,361, and 5,870,272 and further U.S. Pat. Nos. 5,287,076, 5,333,095, 5,905,627 and 5,999,398.

These patents disclose use of discoidal filters and filter arrays in association with conductive pins which are of relatively large scale and difficult to miniaturize without complicating manufacture. It is desirable to further miniaturize and simplify the fabrication of the multi-conductor feedthrough assembly Although feedthrough filter capacitor assemblies of the type described above have performed in a generally satisfactory manner, the manufacture and installation of such filter capacitor assemblies has been relatively time consuming and therefore costly. For example, installation of the discoidal capacitor Into the small annular space between the terminal pin and ferrule as shown in a number of these patents can be a difficult and complex multi-step procedure to ensure formation of reliable, high quality electrical connections.

Other problems have arisen when chip capacitors have been coupled to conductive trace and via pathways of co-fired multi-layer metal-ceramic substrates disclosed in the referenced '652, '358, '891, '476, '435, '926, and '906 patents. The conductive paths of the feedthrough arrays and attached capacitors suffer from high inductance which has the effect of failing to attenuate EMI and other unwanted signals, characterized as "poor insertion loss".

A high integrity hermetic seal for medical implant applications Is very critical to prevent the ingress of body fluids into the IMD. Even a small leak rate of such body fluid penetration can, over a period of many years, build up and damage sensitive internal electronic components. This can cause catastrophic failure of the implanted device. The hermetic seal for medical implant (as well as space and military) applications is typically constructed of highly stable alumina ceramic or glass materials with very low bulk permeability. The above-described feedthroughs formed using metal-ceramic co-fired substrates, however, have not been hermetic because the metal component of the substrate corrodes in body fluids, and the substrates have cracked from stresses that developed from brazing and welding processes.

Withstanding the high temperature and thermal stresses associated with the welding of a hermetically sealed terminal with a premounted ceramic feedthrough capacitor is very difficult to achieve with the '551, '095 and other prior art designs. The electrical/mechanical connection to the outside perimeter or outside diameter of the feedthrough capacitor has a very high thermal conductivity as compared to air. The welding operation typically employed in the medical implant industry to install the filtered hermetic terminal into the IMD case opening can involve a welding operation in very close proximity to this electrical/mechanical connection area. Accordingly, in the prior art, the ceramic feedthrough capacitors are subjected to a dramatic temperature rise. This temperature rise produces mechanical stress in the capacitor due to the mismatch in thermal coefficients of expansion of the surrounding materials.

In addition, in the prior art, the capacitor lead connections must be of very high temperature materials to withstand the high peak temperatures reached during the welding operation (as much as 500° C.). A similar, but less severe, situation is applicable in military, space and commercial applications where similar prior art devices are soldered instead of welded by the user into a bulkhead or substrate. Many of these prior art devices employ a soldered connection to the outside perimeter or outside diameter of the feedthrough capacitor. Excessive and unevenly applied soldering heat has been known to damage such prior art devices. Accordingly, there is a need for a filter capacitor and feedthrough array in a single assembly that addresses the drawbacks noted above in connection with the prior art.

In particular, a capacitive filtered feedthrough array is needed that is subjected to far less temperature rise during the manufacture thereof. Moreover, such an improvement would make the assembly relatively immune to the aforementioned stressful installation techniques.

Moreover, a capacitive filtered feedthrough array is needed which is of simplified construction, utilizing a straightforward and uncomplicated assembly, that can result in manufacturing cost reductions. Of course the new design must be capable of effectively filtering out undesirable EMI. The present invention fulfills these needs and provides other related advantages.

SUMMARY OF THE INVENTION

A capacitive filtered feedthrough assembly is formed in accordance with the present invention in a solid state manner to employ highly miniaturized conductive paths each filtered by a discoid capacitive filter embedded in a capacitive filter array. A non-conductive, co-fired metal-ceramic substrate is formed from multiple layers that supports one or a plurality of substrate conductive paths and it is brazed to a conductive ferrule, adapted to be welded to a case, using a conductive, corrosion resistant braze material. The metal-ceramic substrate is attached to an internally disposed capacitive filter array that encloses one or a plurality of capacitive filter capacitor active electrodes each coupled to a filter array conductive path and at least one capacitor ground electrode. Each capacitive filter array conductive path is joined with a metal-ceramic conductive path to form a feedthrough conductive path. Bonding pads are attached to the internally disposed ends of each feedthrough conductive path, and corrosion resistant, conductive buttons are attached to and seal the externally disposed ends of each feedthrough conductive path. Each capacitor ground electrode is electrically coupled with the ferrule.

Preferably, a plurality of such feedthrough conductive paths are formed, and each capacitive filter comprises a plurality of capacitor active and ground electrodes, wherein the capacitor ground electrodes are electrically connected in common.

Moreover, preferably, a plurality of conductive, substrate ground paths are formed extending through the co-fired metal-ceramic substrate between internally and externally facing layer surfaces thereof and electrically isolated from the substrate conductive paths. The capacitor ground electrodes are coupled electrically to the plurality of conductive, substrate ground paths and to the ferrule.

In addition, preferably, the capacitive filter array conductive paths are formed by solder filling holes extending through the filter array substrate between internally and externally facing array surfaces thereof. The application of the solder also joins the externally facing array surface with the internally facing metal-ceramic substrate layer surface and electrically joins the capacitive filter array conductive paths with the metal-ceramic conductive paths to form the feedthrough conductive paths.

Utilization of an internally grounded, metal-ceramic substrate providing a plurality of conductive substrate paths in stacked, aligned, relation to a capacitive filter array as disclosed herein provides a number of advantages:

A hermetic seal is achieved by brazing a co-fired metal-ceramic substrate with low permeability to a metallic ferrule. The inventive ferrule-substrate braze joint design minimizes the tensile stresses in the co-fired substrate, thus preventing cracking of the co-fired substrate during brazing and welding. In addition, the ferrule has a thin flange which minimizes stress applied to the co-fired substrate during welding. Corrosion of the co-fired metal phase of the substrate is prevented by protecting the exposed metal vias and pads with corrosion resistant metallizations and braze materials.

Because the capacitive filter array Is displaced from the ferrule and supported by the metal-ceramic substrate, the heat imparted to the ferrule flange during welding causes minimal temperature elevation of the capacitive filter array, and does not cause damage to it.

The attachment of the conductive paths of the outward facing capacitive filter surface to the metallized layers of the inward facing surface of the metal-ceramic substrate using reflow soldering provides secure attachment and low resistance electrical connection and simplifies manufacturing. The use of conductive epoxy compounds for adhesion is thereby avoided. Conductive epoxy adhesion layers can bridge the non-conductive ceramic between adjacent conductive paths and cause electrical shorts. And voids can occur in bridging the conductive paths of the metal-ceramic substrate and the capacitive filter elements.

The reflow soldering attachment of the of the conductive paths of the outward facing capacitive filter surface to the metallized layers of the inward facing surface of the metal-ceramic substrate also is advantageous in that the solder flow takes place in an oven under uniformly applied temperature to the entire assembly, thereby avoiding damage that can be caused in hand soldering such parts together.

The capacitor ground electrodes of the discoidal capacitors of the capacitive filter array are electrically coupled together and through the plurality of substrate ground paths of the metal-ceramic substrate and then through the braze to the ferrule. The plurality of substrate ground paths are selected in total cross-section area to provide a total ground via cross-section area that minimizes the inductance of the filtered feedthrough assembly, resulting in favorable insertion loss of EMI and unwanted signals.

Size of the feedthrough is decreased by eliminating the pins, the pin braze joints, and the welds between the pins. The pin-to-pin spacing of two single pin or unipolar feedthroughs is typically on the order of 0.125 inches. The above-described capacitive filtered feedthrough array provides a spacing of 0.050 inches between adjacent conductive paths.

BRIEF DESCRIPTION OF THE DRAWINGS

These and other advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein.

DETAILED DESCRIPTION OF THE PREFERRED EMBODIMENTS OF THE INVENTION

Figure 6:
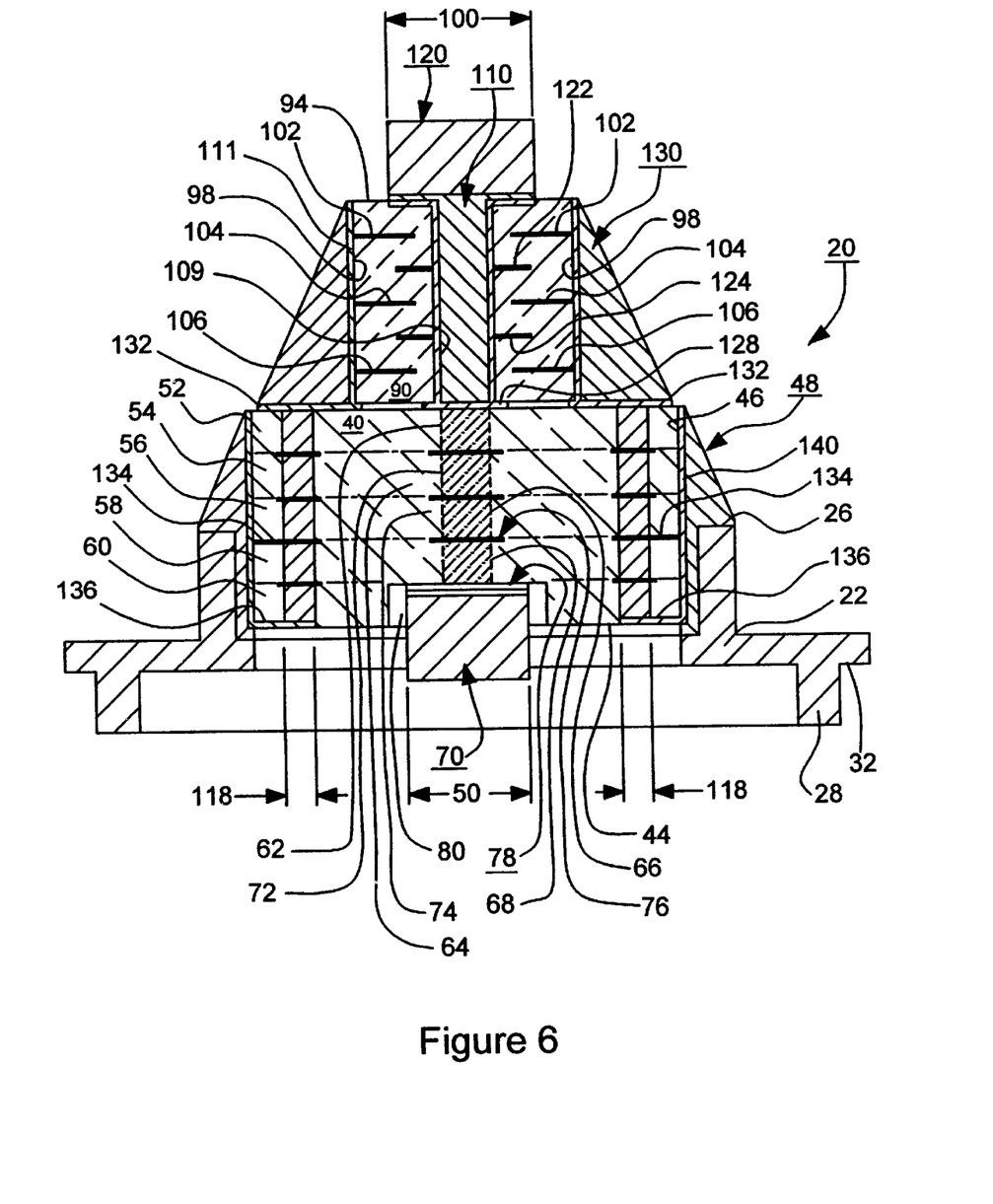
FIG. 6 is a cross-section end view of the filtered feedthrough assembly taken along lines 6—6 of FIG. 3.
Figure 7:
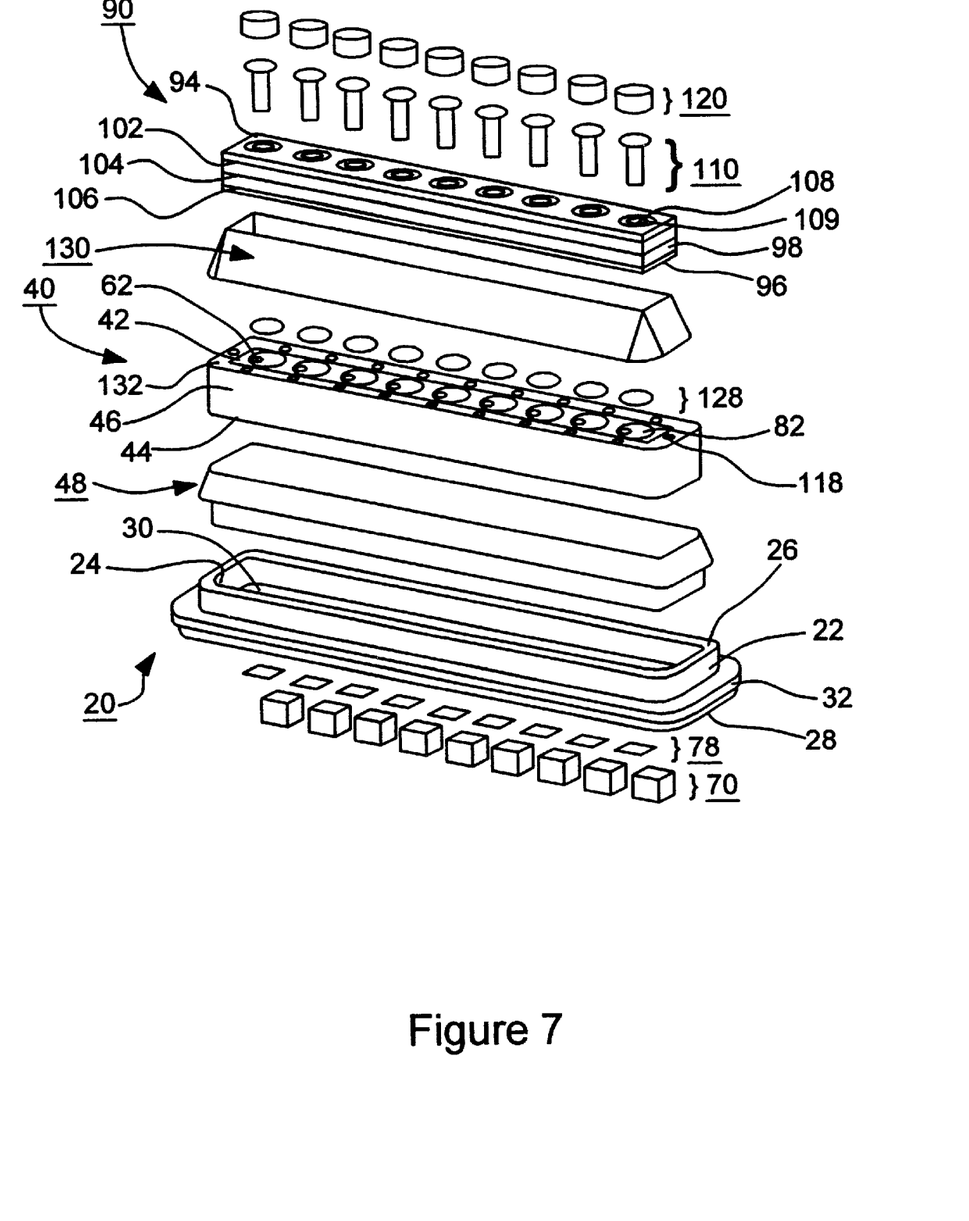
FIG. 7 is an exploded view of the components of the filtered feedthrough assembly of FIGS. 1–6.
Figure 8:
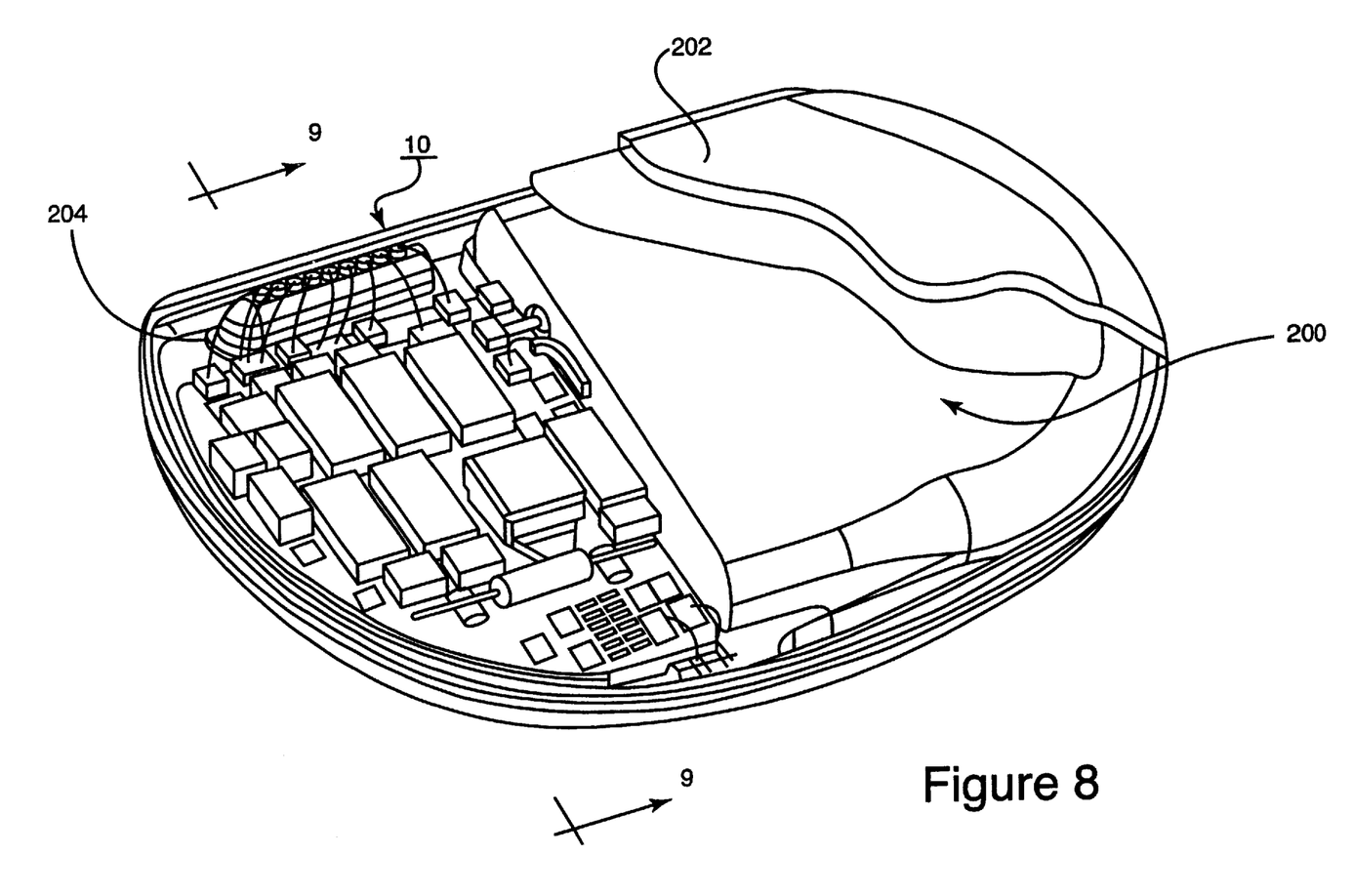
FIG. 8 is a perspective view of the filtered feedthrough assembly of the present invention fitted into an opening of a half portion of the case of a hermetically sealed electronic device showing the externally disposed portion outside the case.
Figure 9:
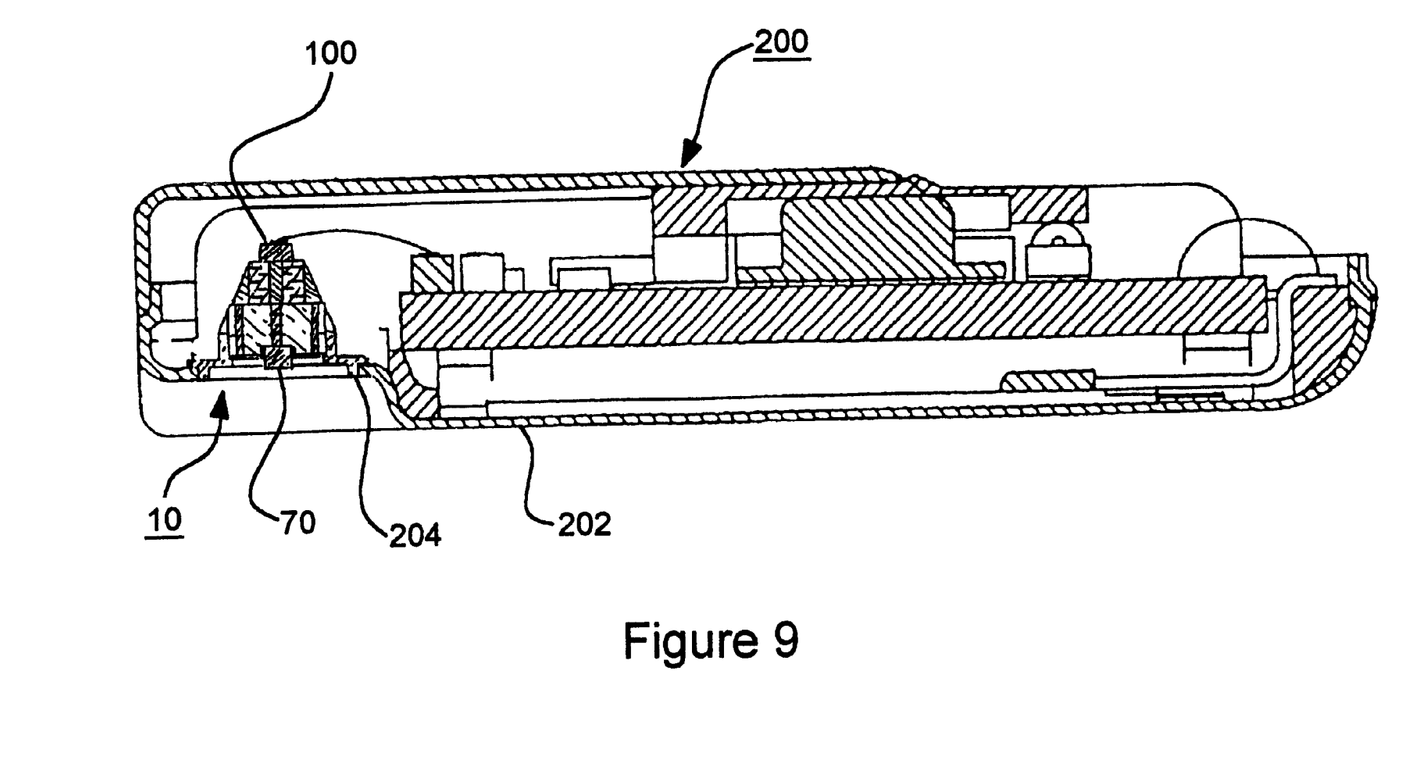
FIG. 9 is a perspective view of the filtered feedthrough assembly of the present invention fitted into the opening of the case half portion of FIG. 7 showing the internally disposed portion inside the case and electrically connected to an electrical component.
Figure 10:
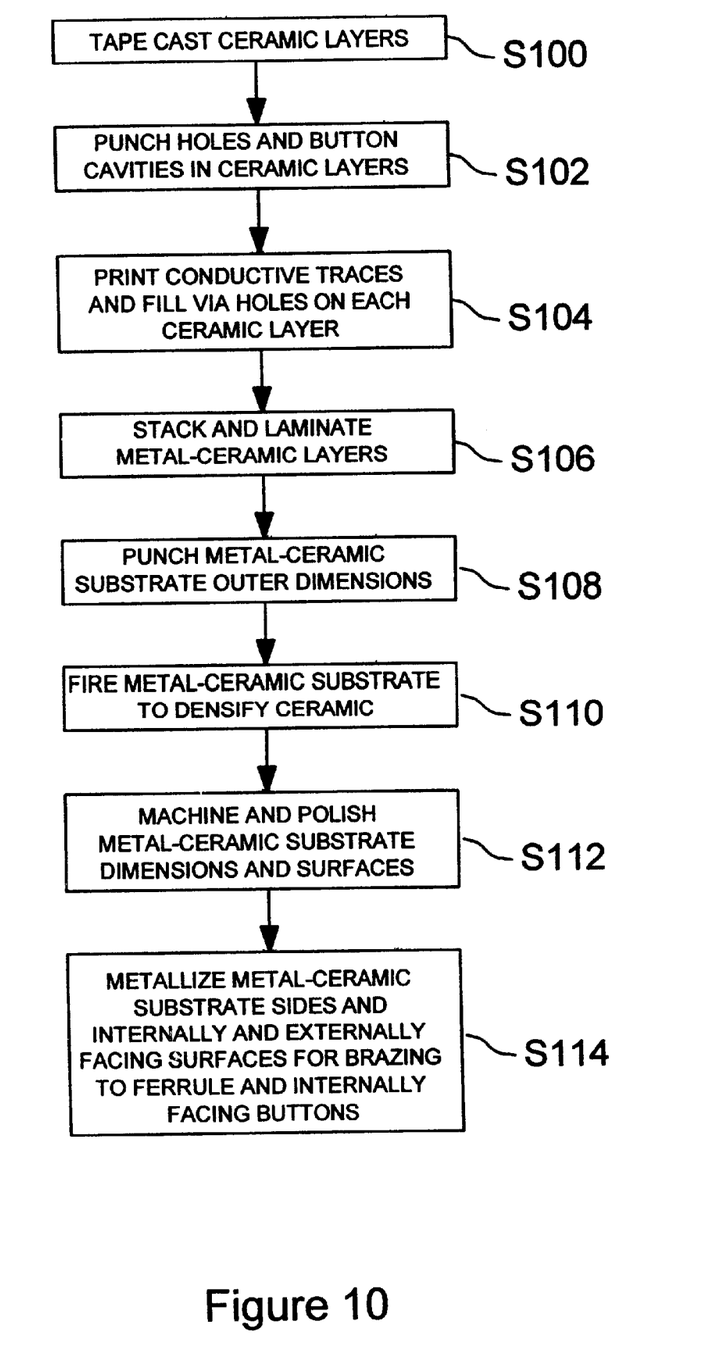
FIG. 10 is a flow chart illustrating the steps of fabricating the multi-layer, co-fired metal-ceramic substrate adapted to be brazed with the capacitive filter array formed in the steps of FIG. 11, the ferrule, and other components in the steps of FIG. 12.
Figure 11:
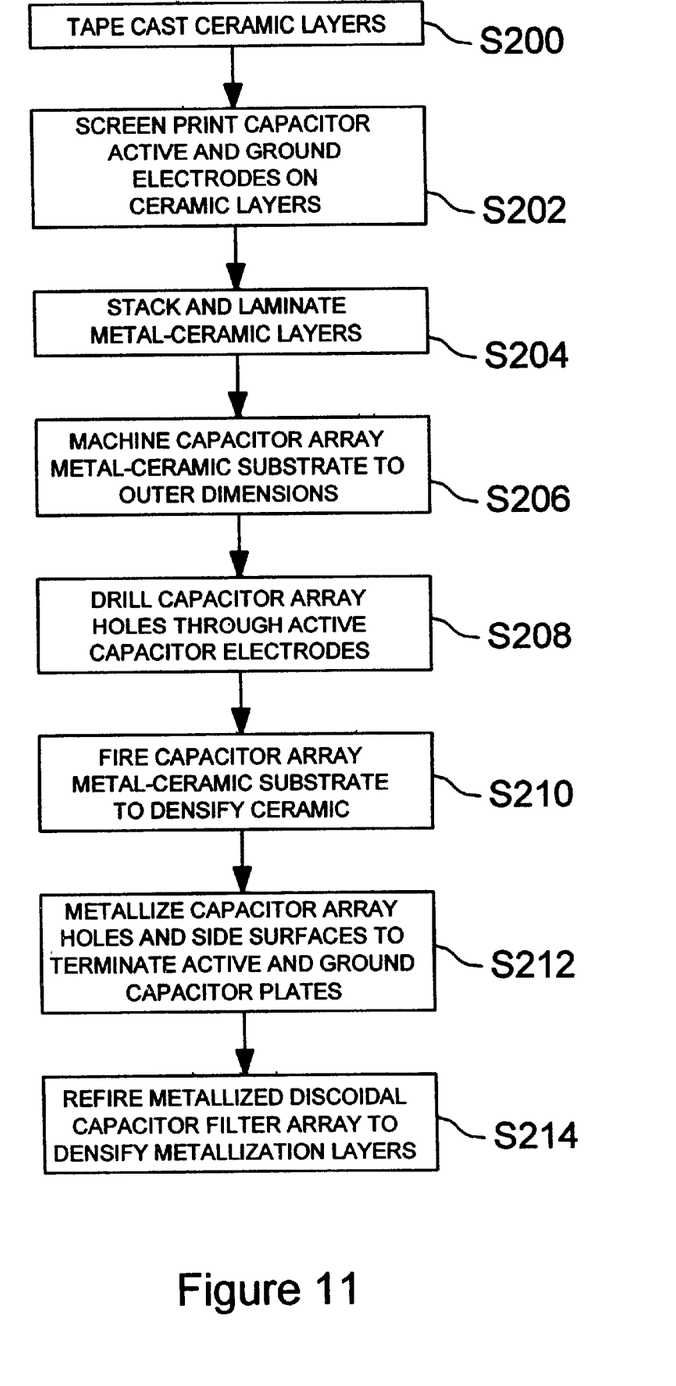
FIG. 11 is a flow chart illustrating the steps of fabricating the capacitive filter array adapted to be brazed with the co-fired metal-ceramic substrate formed in the steps of FIG. 10, the ferrule, and other components in the steps of FIG. 12.
Figure 12:
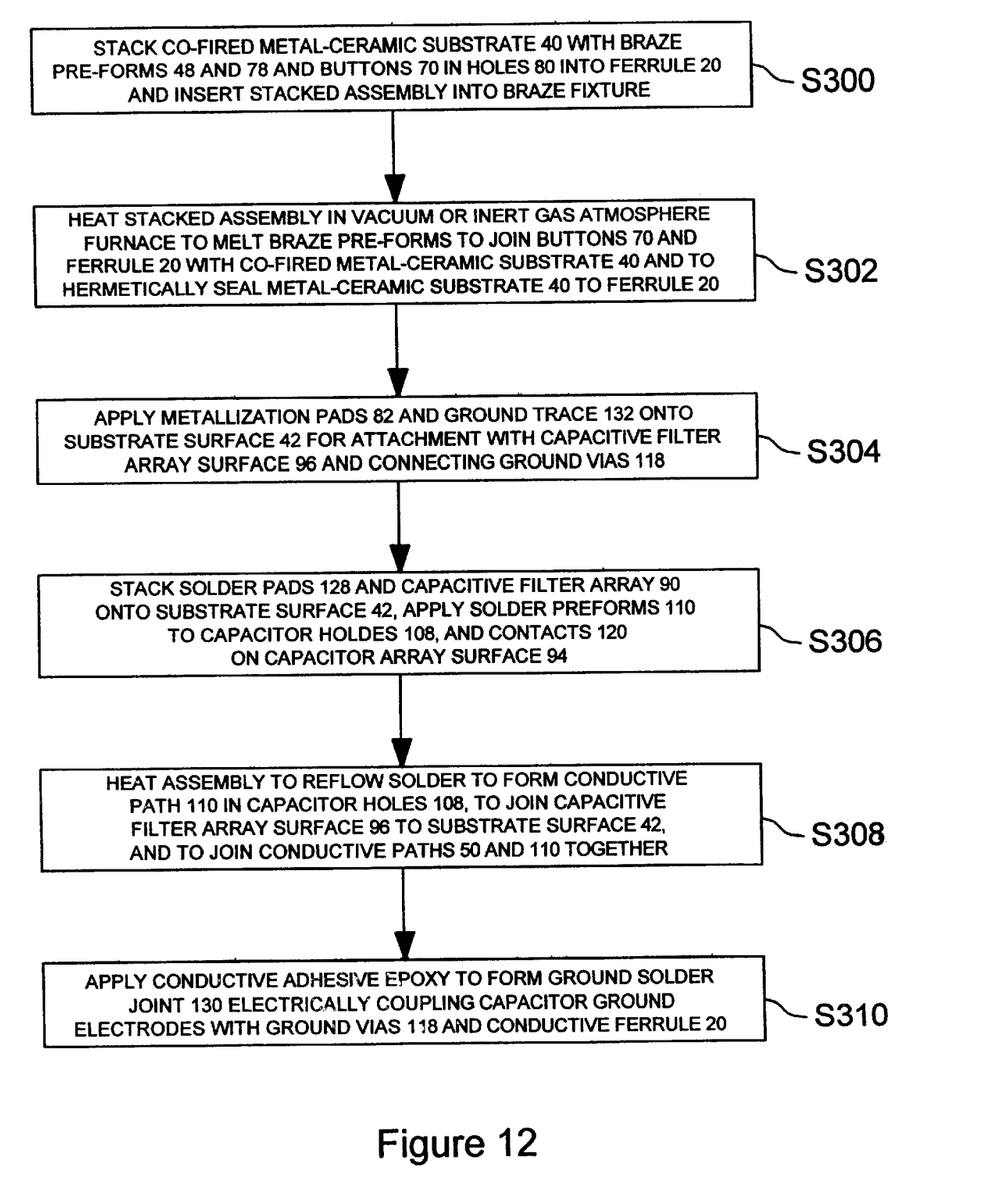
FIG. 12 is a flow chart illustrating the steps of fabricating the filtered feedthrough assembly from the capacitive filter array formed in the steps of FIG. 11, the co-fired metal-ceramic substrate formed in the steps of FIG. 10, the ferrule, and other components.

FIGS. 1–7 depict the filtered feedthrough assembly 10 adapted to be fitted into an opening 204 of a case 202 of a hermetically sealed electronic device 200 as shown in FIGS. 8 and 9 and manufactured in accordance with the flow chart steps of FIGS. 10–12. The feedthrough assembly 10 has an internally disposed portion 12 configured to be disposed inside the case 202 and an externally disposed portion 14 configured to be disposed outside the case 202.

The filtered feedthrough assembly 10 shown in FIGS. 1–9 comprises a electrically conductive ferrule 20 having a ferrule wall 22 with an inner wall surface 24 defining a centrally disposed ferrule opening 30 and extending between opposed internal and external sides 26 and 28. When ferrule 20 is fitted into the case opening 204, the internally facing side 26 is adapted face toward the inside of the case 202, and the externally facing side 28 is adapted face toward the exterior of the case 202. The electrically conductive ferrule 20 further comprises a relatively thin welding flange 32 extending outwardly of the ferrule wall 22 away from the ferrule opening 30 for a predetermined distance defining a flange width FW. The flange 32 is formed to have a relatively thin flange thickness FT for absorbing stress caused by thermal welding energy applied to the ferrule 20 in the process of welding the flange 32 to the case 202 around the case opening 204 as shown in FIGS. 8 and 9.

The ferrule 20 is preferably formed of a conductive material selected from the group consisting of niobium, titanium, titanium alloys such as titanium-6Al-4V or titanium-vanadium, platinum, molybdenum, zirconium, tantalum, vanadium, tungsten, iridium, rhodium, rhenium, osmium, ruthenium, palladium, silver, and alloys, mixtures and combinations thereof. Niobium is the optimal material for forming the ferrule 20 because it has a coefficient of thermal expansion (CTE) that is compatible with the CTE of the substrate 40 so that heat-induced during brazing of the metal-ceramic substrate edge to the ferrule inner wall surface 24 does not damage the substrate 40.

Figure 5:
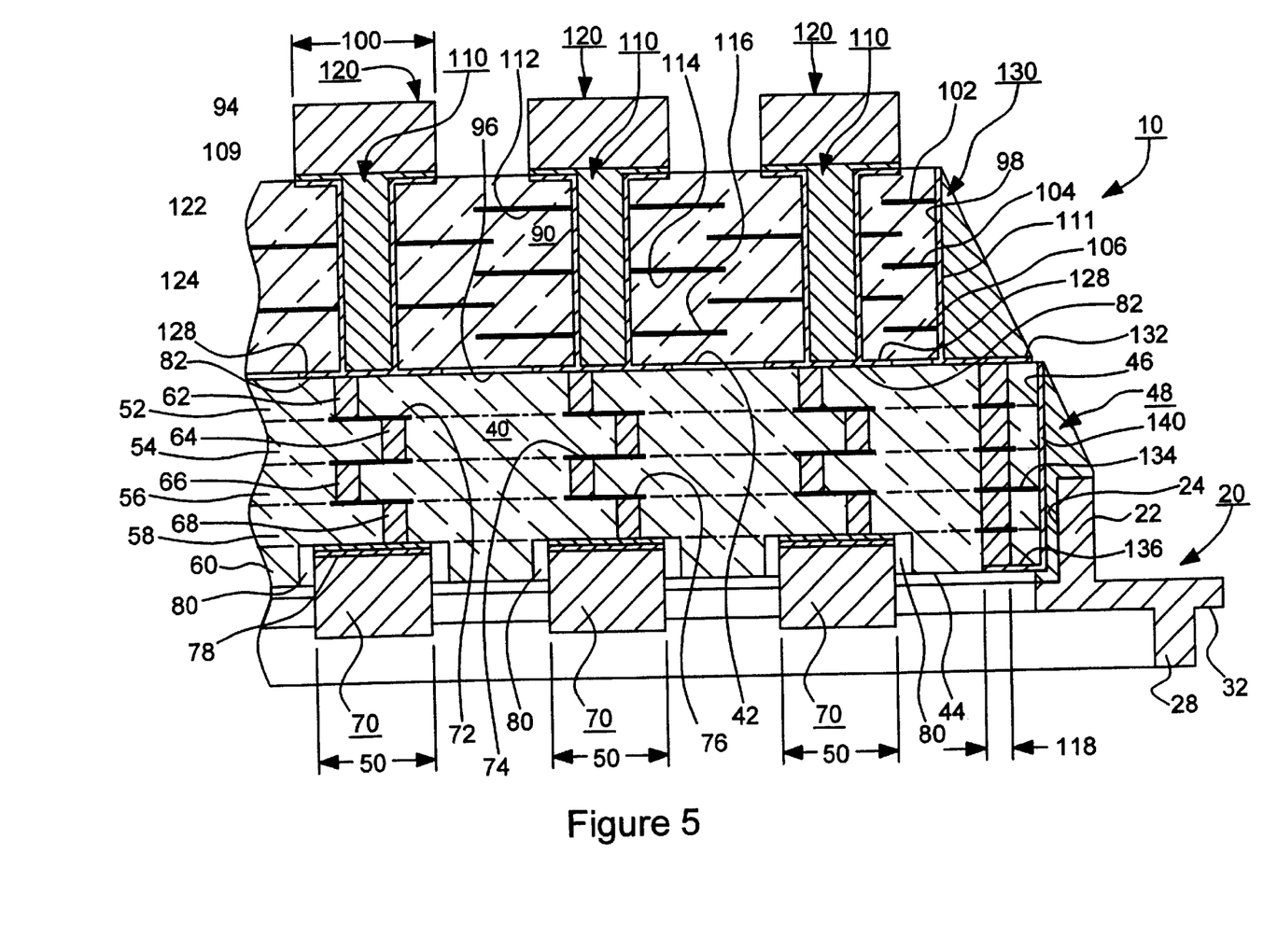
FIG. 5 is an expanded end portion of the cross-section view of FIG. 4

The multi-layer, co-fired metal-ceramic substrate 40 shown in detail in FIGS. 5 and 7 has an internally facing major surface or side 42 and an externally facing major surface or side 44 that are joined by a common substrate edge 46. The substrate 40 is dimensioned and shaped to fit within the ferrule opening 30 with the common substrate edge 46 in close relation to the ferrule inner wall surface 24. The common substrate edge 46 is brazed to the ferrule inner wall surface 24 using a substrate-ferrule braze joint 48.

The metal-ceramic substrate 40 is formed of a plurality of planar ceramic layers 52, 54, 56, 58 and 60. Each ceramic layer is shaped in a green state to have a layer thickness and a plurality of via holes extending therethrough between an internally facing layer surface and an externally facing layer surface. The co-fired metal-ceramic substrate ceramic material comprises one of the group consisting essentially of alumina, aluminum nitride, beryllium oxide, silicon dioxide, and glass-ceramic materials that has a CTE compatible with the CTE of the material of the ferrule.

Figure 1:
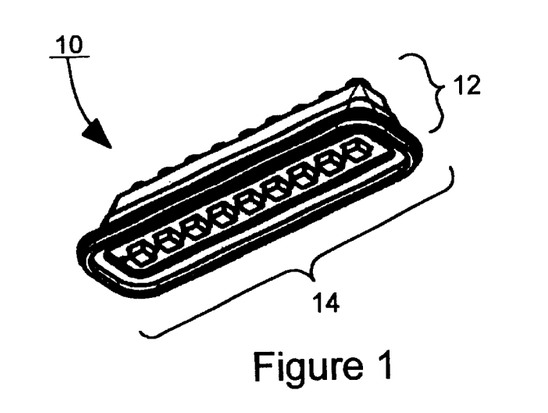
FIG. 1 is a perspective view of the filtered feedthrough assembly of the present invention adapted to be fitted into an opening of a case of a hermetically sealed electronic device showing the externally disposed portion configured to be disposed outside and face outwardly from the case.
Figure 2:
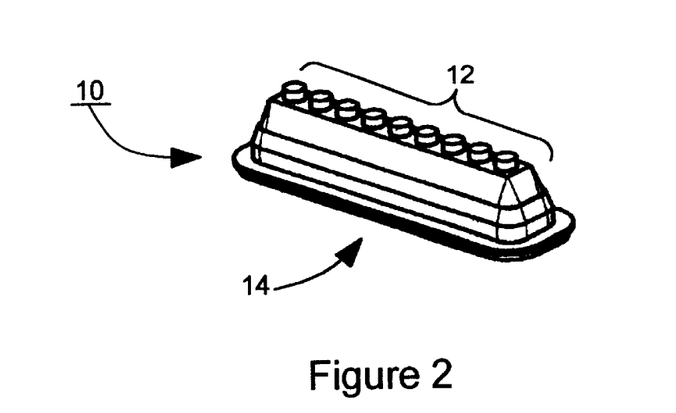
FIG. 2 is a perspective view of the filtered feedthrough assembly of the present invention adapted to be fitted into an opening of a case of a hermetically sealed electronic device showing the internally disposed portion configured to be disposed inside the case and face inward.
Figure 3:
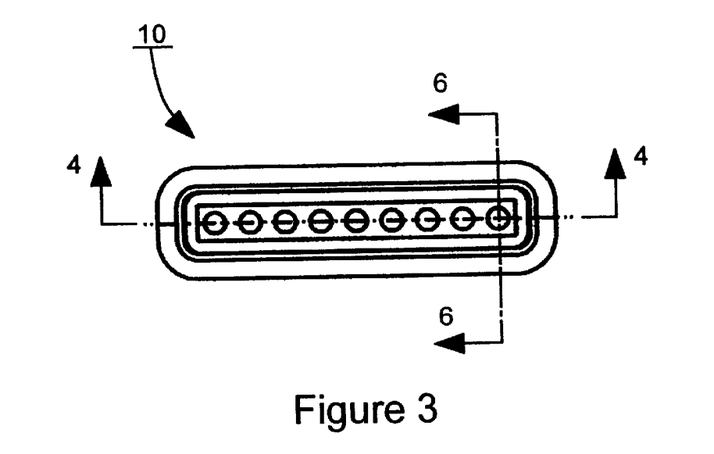
FIG. 3 is a plan view looking toward the internally disposed portion of the filtered feedthrough assembly of the present invention.
Figure 4:
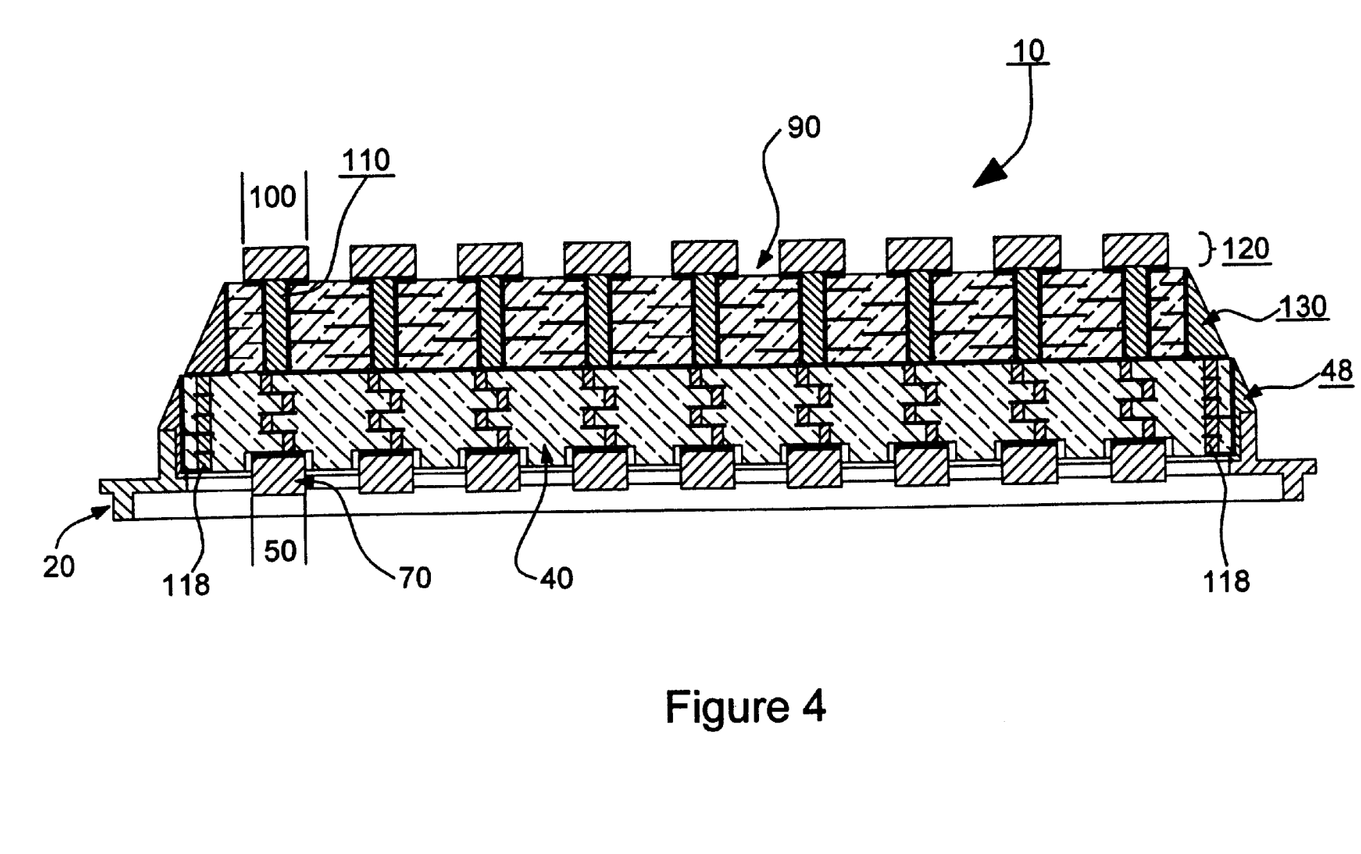
FIG. 4 is a cross-section side view of the filtered feedthrough assembly taken along lines 4—4 of FIG. 3.

A plurality (nine in the depicted example) of conductive paths, e.g. path 50 shown in FIGS. 5 and 6, extend through the layers 52–60 of co-fired metal-ceramic substrate 40 and are electrically isolated from one another by the ceramic material. Conductive path 50 (and all the other conductive paths) comprises a plurality of electrically conductive vias 62, 64, 66, 68 extending through the plurality of layer thicknesses and a like plurality of electrically conductive traces 72, 74 and 76 formed on certain of the internally or externally facing layer surfaces such that the conductive trace 72 joins the conductive vias 62 and 64, the conductive trace 74 joins the conductive vias 64 and 66, and the conductive trace 76 joins the vias 66 and 68 to form the conductive path 50. The layer holes and vias 62–68 filling them are staggered in the elongated direction of the feedthrough assembly 10 as shown in FIGS. 4 and 5 but are aligned in the narrow direction as shown in FIG. 6. The conductive vias and traces are formed of a refractory metal, e.g., tungsten, as described further in reference to FIG. 10.

A further plurality (twenty in the depicted example) of ground paths 118 each comprising substrate ground paths 118 extending through all layers 52-60 spaced apart around the periphery of the co-fired metal-ceramic substrate 40. The ground paths 118 also comprise one or more ground trace, e.g. ground plane traces or layers 132, 134 and 136 shown in FIG. 5, extending peripherally along the substrate layer surfaces from the substrate ground paths 118 to the substrate edge 46. The ground trace 132 assists in making electrical contact with the ground solder joint 130 and with the substrate-ferrule braze joint 48. The ground traces 134 and 136 extend to a metallization layer 140 formed over the substrate edge 46. The number of substrate ground paths 118 substrate ground paths 118 formed in this manner is selected to provide a total ground via cross-section area that minimizes the inductance of the filtered feedthrough assembly 10 resulting in favorable insertion loss of EMI and unwanted signals.

Each such conductive path 50 extends all the way through the substrate 40 between the internally facing side 42 and the externally facing side 44. On the externally facing side 44, ceramic layer 60 is formed in the green state with a plurality of button cavities 80 each aligned with a via 68 of layer 58. A substrate conductor pad or button 70 is fitted within each button cavity 80 of the layer 60 and adhered to via 68 by a button braze joint 78 formed of gold or a nickel-gold alloy. The pads or bonding buttons 70 are preferably formed of a conductive material selected from the group consisting of niobium, platinum or a platinum-iridium alloy, titanium, titanium alloys such as titanium-6Al-4V or titanium-vanadium, molybdenum, zirconium, tantalum, vanadium, tungsten, iridium, rhodium, rhenium, osmium, ruthenium, palladium, silver, and alloys, mixtures and combinations thereof. In this way, a plurality of externally disposed bonding buttons 70 are supported along the externally disposed feedthrough portion 14, and each externally disposed bonding button 70 is electrically conducted with an electrically conductive path 50 of the metal-ceramic substrate 40.

A substrate conductor plated pad 82 is formed of gold or a gold alloy on the internally facing surface of layer 52 and electrically coupled to via 62. A solder layer 128 adheres to plated pad 82 during assembly of the feedthrough assembly 10 described below with reference to FIG. 12. The plurality of ceramic layers are shaped punched with holes, and printed with the traces and vias and assembled together in the ceramic green state, and the assembly is then co-fired from the green state to form the substrate 40 as further described below in reference to FIG. 10.

The discoidal capacitive filter array 90 is formed of a ceramic capacitive filter array substrate 92 having an internally facing filter substrate side 94 and an externally facing filter substrate side 96 joined by a common filter substrate edge 98. The discoidal capacitive filter array 90 is formed with a plurality of discoidal capacitive filters, e.g., capacitive filter 100, that are electrically connected with a respective one of the substrate conductive paths, e.g., conductive path 50, and provide a filtered electrically conductive path between the internally disposed bonding pad 120 and the externally disposed button 70. The number of conductive paths so formed can vary from the nine that are depicted in FIGS. 1–9.

The capacitive filter array substrate 92 is preferably formed of layers of barium titanate and precious metal traces in the manner described below with reference to FIG. 11. The plurality of capacitive filters 100 and the filter array conductive paths 110 associated therewith are formed in and electrically isolated from one another by the ceramic material and extend between the Internally facing filter substrate side 94 and the externally facing filter substrate side 96. Each filter array conducive path 110 is formed of melted solder pre-forms as described below that fill a respective capacitor filter hole 108 extending between the internally facing filter substrate side 94 and an externally facing filter substrate side 96.

Each discoidal capacitive filter 100 comprises at least one capacitor electrode formed within the filter substrate and extending outward from a filter array conductive path 110 in overlapping spaced relation to at least one common ground plate. The number and dielectric thickness spacing of the capacitor electrode sets varies in accordance with the capacitance value and the voltage rating of the discoidal capacitor. The capacitor active and ground electrodes are formed of silver thick films, silver-palladium alloy thick films, or silver-platinum alloy thick films disposed on inner capacitive filter layer surfaces during the fabrication of the capacitive filter array 90. The numbers of capacitor active and ground electrodes, the sizes of each and the spacing and overlapping relation can be varied for each discoidal capacitive filter 100 within the capacitive filter array 90 and between differing models of such capacitive filter arrays 90 to tailor the filter characteristics to the circuitry of the particular IMD. In the depicted example, the capacitive filters 100 either have three capacitor active electrodes 112, 114, 116 or two capacitor active electrodes 122, 124 that are spaced from three ground electrodes 102, 104, 106 that extend inward from the filter substrate edge 98. In operation, the discoidal capacitor permits passage of relatively low frequency electrical signals along the conductive path it is coupled with, while shielding and decoupling/attenuating undesired interference signals of typically high frequency.

The ground solder joint 130, preferably formed of solder or a conductive epoxy, adheres against a metallized layer 111 formed on the filter substrate edge 98 as described below in reference to FIG. 12 that electrically connects the three capacitor ground electrodes 102, 104, 106 together. The ground solder joint 130 also electrically connects the three capacitor ground electrodes 102, 104, 106 to the ferrule 20 through the conductive ground trace 132, the plurality of substrate ground paths 118, and the substrate-ferrule braze joint 48. The ground solder joint 130 can be formed of ABLEBOND.RTM. 8700 electrically conductive silver-filled epoxy adhesive provided by ABLESTIK LABORATORIES of Rancho Dominguez, Calif. Other suitable electrically conductive glue or epoxy-based adhesives and other suitable materials may also be employed in the present invention to form the ground solder joint 130. Such materials include gold or copper-filled epoxies, carbon or graphite-filled epoxies or even electrically conductive plastics acting effectively as adhesive joints after their application and upon cooling, such as at least some of the electrically conductive plastics or polymers disclosed in U.S. Pat. No. 5,685,632. The ground solder joint 130 and the solder layers 128 mechanically join the externally facing filter substrate side to the internally facing substrate side. The solder layers 128 electrically join each filter array conductive path 110 to a substrate conductor pad 82 of each substrate conductive path 50.

The substrate-ferrule braze joint 48 is preferably formed of 99.9% or purer gold or a nickel-gold alloy that adheres to the metallization layer 140 on substrate edge 46 and to the ferrule wall 22 and provides a hermetic seal of the ferrule 20 with the metal-ceramic substrate 40. The substrate-ferrule braze joint 48 may also be formed of: (a) gold alloys comprising gold and at least one of titanium, niobium, vanadium, nickel, molybdenum, platinum, palladium, ruthenium, silver, rhodium, osmium, indium, and alloys, mixtures and thereof; (b) copper-silver alloys, including copper-silver eutectic alloys, comprising copper and silver and optionally at least one of indium, titanium, tin, gallium, palladium, platinum, and alloys, mixtures and combinations thereof; and (c) silver-palladium-gallium alloys.

The filtered feedthrough assembly 10 thus provides a plurality of miniaturized, electrically isolated, and capacitively filtered, electrical conductors formed of conductive path 50 and 110 extending between a respective internal bonding pad 120 of the internally disposed portion 12 and bonding button 70 of the externally disposed portion 14 when the feedthrough assembly 10 is affixed into an opening 204 in the case 202 of the electronic device, e.g., the IMD 200 of FIGS. 8 and 9. The case 202 for an IMD is preferably fabricated of titanium, and the ferrule flange 32 is welded thereto. The ferrule 20 is preferably formed of niobium because niobium has a comparable CTE to the CTE of $AlO_2$ which is a preferred substrate ceramic material. However, the ferrule may be formed of titanium, titanium alloys such as titanium-6Al-4V or titanium-vanadium, platinum, molybdenum, zirconium, tantalum, vanadium, tungsten, iridium, rhodium, rhenium, osmium, ruthenium, palladium, silver, and alloys, mixtures and combinations thereof.

FIG. 10 is a flow chart illustrating the steps of fabricating the multi-layer, co-fired metal-ceramic substrate 40 adapted to be brazed with the capacitive filter array 90 formed in the steps of FIG. 11, the ferrule 20, and other components in the steps of FIG. 12. In step S100 the ceramic layers 52–60 are preferably tape cast from conventional ceramic or low temperature co-fired ceramic, such as alumina, aluminum nitride, beryllium oxide, silicon dioxide, etc., that has a CTE compatible with the CTE of the material of the ferrule 20. Preferably, 88%–96% pure alumina ($AlO_2$) is tape cast using conventional "green sheet" techniques on glass-ceramic or MYLAR support materials. In general, such techniques start with a ceramic slurry formed by mixing a ceramic particulate, a thermoplastic polymer and solvents. This slurry is spread into ceramic sheets of predetermined thickness, typically about 0.006–0.010 inches thick, from which the solvents are volitized, leaving self-supporting flexible green sheets.

In step S102, the holes that will be filled with conductive material to form the vias 62–68 of each conductive path 50 and the aligned ground vias, as well as the button cavities 80 of the layer 60 are made, using any conventional technique, such as drilling, punching, laser cutting, etc., through each of the green sheets from which the ceramic layers 52–60 are formed. The vias 42 may have a size appropriate for the path spacing, with about a 0.004 inch diameter hole being appropriate for 0.020 inch center to center path spacing.

In step S104, the via holes are filled with a paste of refractory metal, e.g., tungsten, molybdenum, or tantalum paste, preferably using screen printing. In step S104, the conductive traces, e.g. traces 72, 74, 76, are also applied to particular surface areas of the ceramic layers 52–60 over the vias. The traces may comprise an electrical conductor, such as copper, aluminum, or a refractory metal paste, that may be deposited on the green sheets using conventional techniques. The traces may be deposited, sprayed, screened, dipped, plated, etc. onto the green sheets. The traces may have a center to center spacing as small as about 0.020 inch (smaller spacing may be achievable as trace forming technology advances) so that a conductive path density of associated vias and traces of up to 50 or more paths per inch may be achieved.

In these ways, the via holes are filled and the conductive traces are applied to the green sheets before they are stacked and laminated in step S106 using a mechanical or hydraulic press for firing. The stacked and laminated ceramic layers are trimmed to the external edge dimensions sufficient to fit within the ferrule opening, taking into account any shrinkage that may occur from co-firing of the stacked layers. In step S110, the assembly of the stacked, laminated and trimmed green sheets is co-fired to drive off the resin and sinter the particulate together into a multi-layer metal-ceramic substrate 40 of higher density than the green sheets forming the layers 52–60. The green sheets shrink in thickness when fired such that a 0.006 inch thick green sheet typically shrinks to a layer thickness of about 0.005 inch. The green sheets may be fired using conventional techniques, with low temperature co-fired ceramic techniques being recommended when copper or aluminum are used.

In step S112, the outer edge 46 and the inward and outward facing substrate surfaces 42 and 44 are machined and polished to size and finish specifications. Then, in step S114, the various regions of the outward facing surface 44 are metallized to form the button braze joints 78 for each conductive path 50 and the band-shaped, ground plane layer 136 electrically connecting all of the substrate ground paths 118 together at the outward facing ends thereof. The substrate edge 46 is also metallized with metallization layer 140. These metallization layers are preferably sputtered films of niobium, titanium, tungsten, molybdenum or alloys thereof. The machining and polishing of the outer edge 46 which is then metallized improves the dimensional tolerances of the co-fired substrate 40 which in turn enables the reliable use of the substrate-ferrule braze joint 48 that is formed in step S300 of FIG. 12.

In a preferred embodiment of the present invention, where pure gold is employed to form the substrate-ferrule braze joint 48, a 25,000 Angstrom thick layer of niobium is preferably sputtered onto substrate edge 46 and on edge bands of the inward facing surface 44 to form the band-shaped, ground plane or trace layers 132 and 136 by vacuum deposition using a Model No. 2400 PERKIN-ELMER.RTM. sputtering system. The niobium layer is most preferably between about 15,000 and about 32,000 Angstroms thick. These metallization layers may not be required if metals such as: (i) gold alloys comprising gold and at least one of titanium, niobium, vanadium, nickel, molybdenum, platinum, palladium, ruthenium, silver, rhodium, osmium, iridium., and alloys, mixtures and thereof; (ii) copper-silver alloys, including copper-silver eutectic alloys, comprising copper and silver and optionally at least one of indium, titanium, tin, gallium, palladium, platinum; or (iii) alloys, mixtures or combinations of (i) or (ii) are employed for the substrate-ferrule braze joint 48.

FIG. 11 is a flow chart illustrating the steps of fabricating the capacitive filter array 90 adapted to be brazed with the co-fired metal-ceramic substrate 40 formed in the steps of FIG. 10, the ferrule 20, and other components in the steps of FIG. 12. The capacitive filter array 90 is also formed of layers of ceramic material, preferably barium titanate, and screen printed, conductive, capacitor active and ground electrodes that are co-fired to form a monolithic structure.

In step S200, the barium titanate ceramic layers are tape cast, and the capacitor active and ground electrodes are screen printed on the surfaces thereof in step S202. The capacitor electrodes are formed of silver thick films, silver-palladium alloy thick films, or silver-platinum alloy thick films. The layers are stacked and laminated using a mechanical or hydraulic press in step S204, and the stacked and laminated layers are machined and drilled to form the capacitor conductive path receiving, capacitive filter holes 108 in steps S206 and S208.

The partly completed capacitor filter array 90 is fired in step S210 to form the monolithic structure. Then, in steps S212 and S214, the edges of the active capacitive filter electrodes 112, 114, 116 or 122, 124 exposed by the capacitor holes 108 and the capacitive filter ground electrodes 102, 104 and 106 are coupled together electrically in common or "terminated". A conductive metal frit that contains one of silver, palladium, platinum, gold and nickel alloys thereof, is placed in the capacitor holes 118 and along the array side 98 and melted to form the termination layers 109 and 111 shown in FIGS. 5 and 6. Most commonly, the conductive frit comprises one of silver, silver-palladium alloy or nickel-gold alloy. Alternatively, the capacitor holes 118 and the array side with layers of nickel and gold. In step S212, the capacitor filter array 90 is fired again to densify the termination layer materials.

FIG. 12 is a flow chart illustrating the steps of fabricating the filtered feedthrough assembly 10 from the capacitive filter array 90 formed in the steps of FIG. 11, the co-fired metal-ceramic substrate 40 formed In the steps of FIG. 10, the ferrule 20, and other components. First, the metal-ceramic substrate 40 is fitted into the ferrule opening and hermetically sealed thereto using the gold or gold alloy substrate-ferrule braze joint 48 and the externally disposed contact buttons 70 are sealed into the button cavities 80. Then, the capacitor filter array 90 is attached to the interior facing surface of the metal-ceramic substrate 40, the capacitor filter conductive paths 110 fill the filter holes 108 using reflow solder techniques, and the internally disposed ground solder joint 130 and the plurality of interior contact pads 120 are attached.

In step S300, the ferrule 20, braze preforms that melt to form the substrate-ferrule braze joint 48, the metal-ceramic substrate 40, and the externally disposed contact buttons 70 in the button cavities 80 are stacked into a braze fixture. Advantageously, these components that are assembled together in step S300 self center and support one another in the braze fixture. This improves the ease of manufacturing and increases manufacturing batch yields. The stacked assembly is subjected to brazing temperatures in a vacuum or inert gas furnace in step S302, whereby the braze preforms melt to form the substrate-ferrule braze joint 48 and the buttons 70 fill the button cavities 80 and adhere to the braze joints 78. As the assembly cools, the ferrule contracts more than the co-fired substrate, which puts the co-fired substrate in a state of compression.

In step S304, the conductive plated pads 82 and the band-shaped, ground plane or trace layer 132 electrically connecting all of the substrate ground paths 118 together at each inward facing end thereof are adhered onto the surface 42 as metallization layers. Each metallization layer preferably comprises sputtered films, first of titanium, then of nickel, and finally of gold, so that a three film metallization layer is formed in each case.

In step S306, the discoid capacitive filter array 90, reflow solder, and the interior contact pads 120 are assembled onto the inward facing surfaces of the sub-assembly formed in step S304, and these components are heated in step S308. The heating causes the solder to flow into and fill the capacitive filter conductive path holes 108 to complete the formation of the capacitive filter conductive paths 110 and the solder pads 128 shown in FIG. 7 and to adhere the internally disposed bonding pad 120. The solder may be an indium-lead or tin-lead alloy, and the internally disposed bonding pads 120 may be formed of Kovar alloy plated with successive layers of nickel and gold. The final layer that is exposed to air and that lead wires are bonded or welded to as shown in FIG. 9 preferably is gold.

In step S310, the ground solder joint 130 is molded around and against the filter substrate edge 98 and the band-shaped, ground plane or trace layer 132. The ground solder joint 130 electrically connects the three ground electrodes 102, 104, 106 together and to the ferrule 20 through the plurality of substrate ground paths 118 and the substrate-ferrule braze joint 48. The ground solder joint 130 also mechanically bonds the discoid capacitive filter array 90 with the multi-layer metal-ceramic substrate 40. Since the ground solder joint 130 does not need to provide a hermetic seal, it may be formed of a number of materials as described above.

In the sputtering steps of the present invention, a DC magnetron sputtering technique is preferred, but RF sputtering techniques may less preferably be employed. A DC magnetron machine that may find application in the present invention is an Model 2011 DC magnetron sputtering device manufactured by ADVANCED ENERGY of Fort Collins, Colo.

The pin-to-pin spacing of two single pin or unipolar feedthroughs is typically on the order of 0.125 inches. The above-described capacitive filtered feedthrough array provides a spacing of 0.050 inches between adjacent conductive paths. The feedthrough assembly 10 can be formed providing the nine capacitively filter array conductive paths within a ferrule 20 that is 0.563 inches long and 0.158 inches wide.

While the present invention has been illustrated and described with particularity in terms of a preferred embodiment, it should be understood that no limitation of the scope of the invention is intended thereby. The scope of the invention is defined only by the claims appended hereto. It should also be understood that variations of the particular embodiment described herein incorporating the principles of the present invention will occur to those of ordinary skill in the art and yet be within the scope of the appended claims.

What is claimed is:

1. A filtered feedthrough assembly adapted to be fitted into an opening of a case of an electronic device, the feedthrough assembly having an internally disposed portion configured to be disposed inside the case and an externally disposed portion configured to be disposed outside the case, the assembly comprising:

an electrically conductive ferrule having a ferrule wall adapted to be fitted into the case opening with an inner wall surface defining a centrally disposed ferrule opening and extending between opposed internally and externally facing ferrule sides;

a multi-layer, co-fired metal-ceramic substrate having opposed internally facing and externally facing substrate surfaces joined by a common substrate edge, the metal-ceramic substrate further comprising:

a plurality of metal-ceramic substrate layers each having internally and externally facing layer surfaces;

a plurality of substrate conductive paths extending through the co-fired metal-ceramic substrate between the internally and externally facing layer surfaces and electrically isolated from one another; and a further plurality of substrate ground paths extending through the co-fired metal-ceramic substrate between the internally and externally facing layer surfaces and electrically isolated from the substrate conductive paths;

means for hermetically sealing the common substrate edge to the ferrule inner wall within the centrally disposed ferrule opening and electrically coupling the plurality of substrate ground paths to the ferrule;

a discoidal capacitive filter array formed of a ceramic capacitive filter substrate having an internally facing filter substrate side and an externally facing filter substrate side joined by a common filter substrate edge, the capacitive filter array substrate further comprising:

a plurality of filter array conductive paths electrically isolated from one another and extending between the internally facing filter substrate side and the externally facing filter substrate side; and a plurality of discoidal capacitor filters each comprising at least one capacitor active electrode formed within the filter substrate and extending outward from a filter array conductive path and a common capacitor ground electrode;

means for mechanically joining the externally facing filter substrate side to the internally facing substrate side and electrically joining each filter array conductive path to a substrate conductive path; and means for electrically coupling the common capacitor ground electrode of the discoidal capacitor filters to the plurality of substrate ground paths;

whereby the filtered feedthrough assembly provides a plurality of miniaturized, electrically isolated, and capacitively filtered, feedthrough conductive paths with low inductance each comprising a substrate conductive path joined to a filter array conductive path and extending between the internally disposed portion and the externally disposed portion when the feedthrough assembly is affixed into an opening in the case of the electronic device.

2. The filtered feedthrough assembly of claim 1, wherein the case of the electronic device and the ferrule are formed of metallic materials amenable to being welded together, the electrically conductive ferrule further comprises a welding flange extending outwardly of the ferrule wall away from the ferrule opening for a predetermined distance defining a flange width, and the flange formed with a stress relieving thickness for absorbing stress caused by thermal welding energy applied to the ferrule and flange in the process of welding the flange to the case.

3. The filtered feedthrough assembly of claim 2, wherein the co-fired metal-ceramic substrate ceramic material comprises one of the group consisting essentially of alumina, aluminum nitride, beryllium oxide, and silicon dioxide that has a coefficient of thermal expansion (CTE) compatible with the CTE of the material of the ferrule.

4. The filtered feedthrough assembly of claim 3, wherein the ferrule is formed of a conductive material selected from the group consisting of niobium, titanium, titanium alloys such as titanium-6Al-4V or titanium-vanadium, platinum, molybdenum, zirconium, tantalum, vanadium, tungsten, iridium, rhodium, rhenium, osmium, ruthenium, palladium, silver, and alloys, mixtures and combinations thereof.

5. The filtered feedthrough assembly of claim 1, wherein:

the metal-ceramic substrate further comprises a plurality of planar ceramic layers shaped in a green state to have a layer thickness and a plurality of substrate conductive path via holes and common ground via holes extending therethrough between an internally facing layer surface and an externally facing layer surface, the plurality of ceramic layers assembled together and co-fired from the green state to form the substrate;

each of the plurality of substrate conductive paths extending through the co-fired metal-ceramic substrate between the internally and externally facing layer surfaces and electrically isolated from one another further comprise a plurality of electrically conductive vias extending through via holes of the plurality of layer thicknesses and a plurality of electrically conductive traces formed on certain of the internally or externally facing layer surfaces such that the conductive traces join the conductive vias to form each substrate conductive path; and each of the further plurality of substrate ground paths extending through the co-fired metal-ceramic substrate between the internally and externally facing layer surfaces comprise a plurality of electrically conductive vias extending through via holes of the plurality of layer thicknesses and at least one conductive trace formed on certain of the internally or externally facing layer surfaces and extending to the substrate edge to enable electrical joinder of the ground vias in common and to the ferrule through the means for hermetically sealing the common substrate edge to the ferrule inner wall within the centrally disposed ferrule opening.

6. The filtered feedthrough assembly of claim 5, wherein the means for hermetically sealing the common substrate edge to the ferrule inner wall within the centrally disposed ferrule opening and electrically coupling the plurality of substrate ground paths to the ferrule comprises a substrate-ferrule braze joint formed of a conductive braze material.

7. The filtered feedthrough assembly of claim 5, wherein each of the plurality of substrate conductive paths extending through the co-fired metal-ceramic substrate between the internally and externally facing layer surfaces further comprise:

a substrate conductor braze pad on the substrate internally facing side comprising part of the means for mechanically joining the externally facing filter substrate side to the internally facing substrate side and electrically joining each filter array conductive path to a substrate conductive path;

a substrate conductor braze pad on the substrate externally facing side; and an externally disposed bonding button mechanically supported on the externally facing metal-ceramic substrate side and electrically connected with an electrical path of the metal-ceramic substrate through the braze pad on the substrate externally facing side.

8. The filtered feedthrough assembly of claim 7, wherein the externally disposed bonding buttons are formed of a conductive material selected from the group consisting of niobium, platinum or a platinum-iridium alloy, titanium, titanium alloys such as titanium-6Al-4V or titanium-vanadium, molybdenum, zirconium, tantalum, vanadium, tungsten, iridium, rhodium, rhenium, osmium, ruthenium, palladium, silver, and alloys, mixtures and combinations thereof.

9. The filtered feedthrough assembly of claim 7, wherein the exterior facing surface of the metal-ceramic substrate is formed with a plurality of spaced apart button cavities aligned with the plurality of substrate conductor paths extending through the externally facing ceramic layer of the metal-ceramic substrate, each conductor hole receiving a substrate conductor braze pad and an externally disposed bonding button therein.

10. The filtered feedthrough assembly of claim 7, wherein the substrate conductive paths are formed of a conductive paste applied by screen printing to said ceramic layers in the green state to form the traces and fill the via holes, the conductive paste selected from the group consisting of copper, tungsten, molybdenum and gold.

11. The filtered feedthrough assembly of claim 7, wherein:
   each filter array conductive path further comprises a filter array hole extending between the internally facing filter substrate side and the externally facing filter substrate side and through at least one capacitor active electrode; and
   the means for mechanically joining the externally facing filter substrate side to the internally facing substrate side and electrically joining each filter array conductive path to a substrate conductive path comprises reflow solder filling the filter array holes and mechanically bonded with the substrate conductor braze pads on the substrate internally facing side, whereby the reflow solder within each filter array hole forms at least part of a filter array conductive path.

12. The filtered feedthrough assembly of claim 11, wherein the filter array conductive paths further comprise a plurality of internally disposed bonding pads adhering to the reflow solder filling the plurality of filter array holes on the internally facing side of the capacitive filter array.

13. The filtered feedthrough assembly of claim 12, wherein the internally disposed bonding pads are formed of a conductive material selected from the group consisting of copper, nickel, gold and aluminum and alloys, mixtures and combinations thereof.

14. The filtered feedthrough assembly of claim 7, wherein:
   each capacitive filter comprises a plurality of capacitor active electrodes formed within the filter substrate and extending outward from a filter array conductive path, a further plurality of capacitor ground electrodes formed within the filter substrate and extending inward from the filter substrate edge, and a termination layer overlying the filter substrate edge electrically coupling the capacitor ground electrodes together.

15. The filtered feedthrough assembly of claim 14, wherein:
   each filter array conductive path further comprises a filter array hole extending between the internally facing filter substrate side and the externally facing filter substrate side and through the plurality of capacitor active electrodes, and a hole metallization layer within the hole electrically coupling the capacitor active electrodes together; and
   the means for mechanically joining the externally facing filter substrate side to the internally facing substrate side and electrically joining each filter array conductive path to a substrate conductive path comprises reflow solder filling the filter array holes and mechanically bonded with the hole metallization layer and the substrate conductor braze pads on the substrate internally facing side, whereby the reflow solder within each filter array hole forms at least part of a filter array conductive path.

16. The filtered feedthrough assembly of claim 1, wherein:
   the filter conductive paths further comprise a plurality of internally disposed bonding pads supported along the Internally facing filter substrate side, each internally disposed bonding pad electrically conducted with a filter array conductive path of the capacitive filter array; and
   the substrate conductive paths further comprise a plurality of externally disposed bonding buttons supported along the externally facing metal-ceramic substrate side, each externally disposed bonding button electrically conducted with a substrate conductive path.

17. The filtered feedthrough assembly of claim 16, wherein the internally disposed bonding pads are formed of a conductive material selected from the group consisting of copper, nickel, gold and aluminum and alloys, mixtures and combinations thereof.

18. The filtered feedthrough assembly of claim 16, wherein the externally disposed bonding buttons are formed of a conductive material selected from the group consisting of niobium, platinum or a platinum-iridium alloy, titanium, titanium alloys such as titanium-6Al-4V or titanium-vanadium, molybdenum, zirconium, tantalum, vanadium, tungsten, iridium, rhodium, rhenium, osmium, ruthenium, palladium, silver, and alloys, mixtures and combinations thereof.

19. A filtered feedthrough assembly adapted to be fitted into an opening of a case of an electronic device, the feedthrough assembly having an internally disposed portion configured to be disposed inside the case and an externally disposed portion configured to be disposed outside the case, the assembly comprising:
   an electrically conductive ferrule having a ferrule wall adapted to be fitted into the case opening with an inner wall surface defining a centrally disposed ferrule opening and extending between opposed internally and externally facing ferrule sides;
   a multi-layer, co-fired metal-ceramic substrate having opposed internally facing and externally facing substrate surfaces joined by a common substrate edge, the metal-ceramic substrate further comprising a plurality of metal-ceramic substrate layers each having internally and externally facing layer surfaces and a plurality of substrate conductive paths extending through the co-fired metal-ceramic substrate between the internally and externally facing layer surfaces and electrically isolated from one another;
   means for hermetically sealing the common substrate edge to the ferrule inner wall within the centrally disposed ferrule opening and electrically coupling the plurality of substrate ground paths to the ferrule;
   a discoidal capacitive filter array formed of a ceramic capacitive filter substrate having an internally facing filter substrate side and an externally facing filter substrate side joined by a common filter substrate edge, the capacitive filter array substrate further comprising:
      a plurality of filter array conductive paths electrically isolated from one another and extending between the internally facing filter substrate side and the externally facing filter substrate side each formed of reflow solder filling a; filter array hole; and
      a plurality of discoidal capacitor filters each comprising at least one capacitor active electrode formed within the filter substrate and extending outward from a filter array conductive path and a common capacitor ground electrode;
   means for mechanically joining the externally facing filter substrate side to the internally facing substrate side and electrically joining each filter array conductive path to a substrate conductive path comprising the reflow solder forming the plurality of filter array conductive paths; and
   means for electrically coupling the common capacitor ground electrode of the discoidal capacitor filters to the ferrule;

whereby the filtered feedthrough assembly provides a plurality of miniaturized, electrically isolated, and capacitively filtered, feedthrough conductive paths each comprising a substrate conductive path joined to a filter array conductive path and extending between the internally disposed portion and the externally disposed portion when the feedthrough assembly is affixed into an opening in the case of the electronic device.

* * * * *